United States Patent [19]

Fleckenstein et al.

[11] Patent Number: 5,180,858

[45] Date of Patent: Jan. 19, 1993

[54] PROCESS FOR THE CATALYTIC HYDROGENATION OF LIQUID FATTY ACID METHYL ESTERS

[75] Inventors: Theo Fleckenstein, Hilden; Gerd Goebel, Cologne; Franz-Josef Carduck, Haan; Guenther Demmering; Hans-Peter Kubersky, both of Solingen, all of Fed. Rep. of Germany

[73] Assignee: Henkel Kommanditgesellschaft auf Aktien, Duesseldorf, Fed. Rep. of Germany

[21] Appl. No.: 768,882

[22] PCT Filed: Apr. 17, 1990

[86] PCT No.: PCT/EP90/00597

§ 371 Date: Oct. 24, 1991

§ 102(e) Date: Oct. 24, 1991

[87] PCT Pub. No.: WO90/12775

PCT Pub. Date: Nov. 1, 1990

[30] Foreign Application Priority Data

Apr. 24, 1989 [DE] Fed. Rep. of Germany ....... 3913387

[51] Int. Cl.$^5$ .................... C07C 29/149; C07C 31/04; C07C 31/125
[52] U.S. Cl. .................................. 568/885; 568/864
[58] Field of Search ......................................... 568/885

[56] References Cited

U.S. PATENT DOCUMENTS

| | | | |
|---|---|---|---|
| 3,341,610 | 9/1967 | Dunlop et al. | 568/881 |
| 4,960,960 | 10/1990 | Harrison et al. | 568/881 |
| 5,043,485 | 8/1991 | Fleckenstein et al. | 568/885 |

FOREIGN PATENT DOCUMENTS 975134  11/1964  United Kingdom ............... 568/885

Primary Examiner—Joseph E. Evans
Attorney, Agent, or Firm—Ernest G. Szoke; Wayne C. Jaeschke; Henry E. Millson, Jr.

[57] ABSTRACT

The invention relates to a process for the catalytic hydrogenation of liquid saturated and unsaturated $C_{6-24}$ fatty acid methyl esters for the production of saturated fatty alcohols and methanol in the presence of gaseous hydrogen and hydrogenation catalysts under pressures of 50 to 300 bar and at temperatures in the range from 160° to 250° C., characterized in that the hydrogenation reaction is carried out in a tube bundle reactor in which isothermal conditions are established by a cooling or heating fluid, the liquid phase and gas phase being passed together as a co-current trickle phase over catalyst packings in the individual tubes of the reactor without any back-mixing, and in that the load per unit volume of the reaction is between 0.2 and 2.5 liters starting material per liter reactor volume per hour and the load per unit area of each individual tube of the reactor is between 1.5 and 24 m$^3$ starting material per m$_2$ reactor cross-section per hour and the reaction parameters of temperature and pressure and correspondingly adapted to the particular activity of the catalyst.

30 Claims, No Drawings

PROCESS FOR THE CATALYTIC HYDROGENATION OF LIQUID FATTY ACID METHYL ESTERS

This invention relates to a process for the catalytic hydrogenation of liquid saturated and unsaturated $C_{6-24}$ fatty acid methyl esters for the production of saturated fatty alcohols and methanol in the presence of gaseous hydrogen and hydrogenation catalysts under pressures of 50 to 300 bar and at temperatures in the range from 160° to 250° C.

Hitherto, trickle bed reactors, which are essentially shaft reactors up to 2 m in diameter and between 5 m and 10 m in length, have been used for processes of the type in question carried out in industrial plants. The catalyst required for the hydrogenation is distributed as a random packing in the reactor (Ullmann's Enzyklopädie der Technischen Chemie, 4th Edition, Vol. 11, pages 433 and 434). In these reactors, the reaction is carried out adiabatically, i.e. in the mostly exothermic reactions, the temperature increases along the catalyst packing. However, since the selectivity of most types of catalyst is largely dependent on temperature, changes in the reaction mechanism can occur as a result of temperature changes in the reactor so that mostly unwanted secondary or consecutive reactions can therefore take place. Moreover, excessive temperatures can lead to irreversible catalyst damage.

In addition, there is an unfavorably broad residence time distribution in known shaft reactors despite the uniform distribution of liquid over the cross-section This reduces the degree of utilization of the reactor.

Although it is known that, to limit the increase in temperature, the gas phase may be passed through the reactor in a large excess or several reactors arranged in series with intermediate cooling may be used, this method of temperature control is unsuitable for the hydrogenation of fatty acid methyl ester because the unwanted consecutive reactions cannot be ruled out in this way and, if certain temperatures are increased, the catalysts can suffer losses of activity through recrystallization and structural changes.

It is also known that catalytic reactions can be carried out in an isothermally operated tube bundle reactor (cf. Chemie-Technik, Vol. 4 (1975), No. 12, pages 439 to 441). In the so-called Bayer cold hydrogenation process, catalytic hydrogenations are carried out substantially isothermally at low temperatures so that the catalyst is not subjected to any temperature variations and there is no danger of overheating. However, the reaction described in this literature reference is by no means a critical hydrogenation reaction because the reaction product is not subjected to the further reaction to this extent, if at all, so that—if necessary—unreacted fractions can be recycled; even an extended residence time under hydrogenation conditions does not damage the product.

The problem addressed by the present invention was to provide a process of the type mentioned at the beginning in which considerably higher throughputs by comparison with conventional processes can be achieved, particularly in the hydrogenation of unsaturated fatty acid methyl esters and short-chain fatty acid methyl esters having chain lengths of 6 to 10 carbon atoms.

According to the invention, this problem is solved by the process mentioned at the beginning in that the hydrogenation reaction is carried out in a tube bundle reactor in which isothermal conditions are established by a cooling or heating fluid, the liquid phase and gas phase being passed together as a co-current trickle phase over catalyst packings in the individual tubes of the reactor without any back-mixing, and in that the load per unit volume of the reactor is between 0.2 and 2.5 liters starting material per liter reactor volume per hour and the load per unit area of each individual tube of the reactor is between 1.5 and 24 $m^3$ starting material per $m^2$ reactor cross-section per hour and the reaction parameters of temperature and pressure are correspondingly adapted to the particular activity of the catalyst. In the process according to the invention, throughputs up to 3 times higher than in processes using conventional reactors are achieved. This means a reduction in the reactor volume by the same factor. The heat of reaction is largely dissipated through the wall of the reactor so that substantially isothermal operation is possible. The catalyst is thus preserved, works more selectively and has a longer useful life.

Whereas, in conventional shaft reactors, large quantities of hydrogen recycle gas are necessary for reducing exothermy and for maintaining favorable flow conditions, distinctly smaller quantities of recycle gas are sufficient for the tube bundle reactor despite the higher throughputs. In addition, a reduction in the recycle gas stream has an extremely favorable effect on the investment costs of the plant. In addition, the shorter overall length of the tube bundle reactor means that the pressure drop in the reactor is reduced which saves compression energy.

Under these process conditions, the hydrogenation reaction can be controlled in such a way that the reaction is stopped at the stage of the desired reaction products. This control of the reaction is achieved through the fact that the fluid phases are passed without back-mixing through the catalyst packings in the individual tubes of the reactor with a definite residence time. At the same time, the reaction parameters of temperature and pressure are adapted to one another in accordance with the particular activity of the catalyst until the desired product yields are obtained. The isothermal temperature control in the tube bundle reactor ensures that only the desired reaction mechanisms come into play.

Although DE 37 24 257 A1 describes a process for the hydrogenation of fatty acid methyl ester mixtures, the Examples relate solely to laboratory tests for determining the activity of the catalyst described therein. No conclusions can be drawn therefrom as to the industrial hydrogenation process according to the present invention.

According to the invention, the specific recycle gas volume is preferably from 1,200 to 6,500 and more preferably from 2,000 to 3,000 $Nm^3/Nm^3$ ester/h.

In one advantageous embodiment of the invention, which is concerned with preventing separation, the internal diameter of the individual tubes of the reactor is selected between 25 and 400 mm, preferably between 30 and 100 mm and more preferably between 40 and 70 mm and the mobile phases are passed through the catalyst packing in plug flow characteristic. Plug flow characteristic means that the flow rates both of the gas phase and of the liquid phase are the same in all the tubes of the reactor so that a narrow residence time distribution is obtained. This design of the individual reactor tubes ensures that the catalyst is uniformly wetted so that no uncontrolled reactions can occur. This guarantees precise control of the reaction to obtain the desired reaction product.

The invention is illustrated by the following Table of Examples.

|  | 1 | 2 | 3 | Comparison Example |
|---|---|---|---|---|
| Starting material | C12–C18 fatty acid methyl ester (dist.) | | | |
| Reactor type | Tube reactor isothermal | Tube reactor isothermal | Tube bundle reactor isothermal | Shaft reactor adiabatic |
| Tube arrangement | — | — | Parallel | In series |
| No. of tubes | 1 | 1 | 31 | 2 |
| Length (m) | 6 | 6 | 6.5 | 7.25 |
| Diameter (internal) (mm) | 63 | 63 | 63.5 | 1340 |
| Cata-type | CuZn | CuZn | CuZn | CuZn |
| Form | Cyl. Tabl. | Cyl. Tabl. | Cyl. Tablets | Cyl. Tablets |
| Size (mm) | 3 × 3 | 4 × 4 | 4 × 4 | 6 × 6 |
| React. Pressure | 250 | 250 | 250 | 250 |
| Entry Temp. (°C.) | 228 | 224 | 226 | 225 |
| Exit Temp. (°C.) | 227 | 224 | 226 | 240 |
| Cata. volume (l) | 16 | 16 | 600 | 17000 |
| Feed throughp. (l/h) | 24 | 24 | 1600 | 8000 |
| LHSV ($h^{-1}$) | 1.5 | 1.5 | 1.5 | 0.4706 |
| Methanol throughput (l/h) | — | — | — | 900 |
| Recycle gas (pressure $m^3$/h) | 1.6 | 0.5 | 15 | 432 |
| Recycle gas (pressure $m^3/m^3$ ester/h) | 66.67 | 20.84 | 9 | 54 |
| Product-spec S.V. | 1.2 | 1.2 | 1.2 | 1.2 |
| HC (% by wt.) | 0.3–0.5 | 0.3–0.5 | 0.3–0.5 | 0.5–0.7 |
| Cata. depreciation | <0.1% | — | <0.13% | 0.15% |

In one particularly suitable embodiment, the load per unit volume is adjusted to values of 0.3 to 2.0 liters starting material per liter reactor volume per hour. At the same time, the load per unit area of each individual reactor tube is advantageously adjusted to values of 1.5 to 15 $m^3$ starting material per $m_2$ reactor cross-section per hour. These particular process conditions provide for particularly exact control of the reaction.

In another preferred embodiment of the invention, the maximum temperature increase in the reaction zone is adjusted to values of at most 5° C. by internal cooling through an excess of hydrogen and/or by external cooling through the cooling fluid. This very precise temperature control ensures that no unwanted consecutive reactions occur and that the catalyst is not damaged by heat.

In another embodiment of the invention, the process is carried out at temperatures of 180° to 250° C. and under pressures of 150 to 280 bar. These reaction parameters have proved to be particularly favorable.

In another embodiment, the individual reactor tubes are uniformly charged with liquid phase to an accuracy of 5% through a distributor. This ensures that a uniform reaction takes place in all the reaction tubes so that a uniform reaction product is formed.

In a further embodiment, the individual reactor tubes are uniformly charged with liquid phase through a two-stage liquid distributor. A particularly narrow residence time distribution of the gas and liquid phases is achieved in this way.

Finally, in another embodiment, no methanol is added to the starting product because, in the process according to the invention, there is no need to add methanol to the starting material. The fact that heat can be directly dissipated provides for more gentle reduction of the catalyst and increased safety in operation.

We claim:

1. In a process for the catalytic hydrogenation of liquid saturated and unsaturated $C_{6-24}$ fatty acid methyl esters for the production of saturated fatty alcohols and methanol in the presence of gaseous hydrogen and a hydrogenation catalyst under a pressure of from about 50 to about 300 bar and at a temperature in the range of from about 160 to about 250° C., the improvement wherein the process (a) is carried out under substantially isothermal conditions in a multiplicity of discrete tubular reaction zones (b) the reaction mixture comprises both a liquid phase and a gas phase, and the liquid phase and the gas phase are passed together in co-current flow over a stationary catalyst in each reaction zone without back-mixing, (c) between about 0.2 and about 2.5 liters of ester per liter of tubular reaction zone per hour is employed, (d) between about 1.5 and about 24 $m^3$ of ester is used per $m^2$ cross section of tubular reaction zone per hour, (e) the temperature and pressure in the tubular reaction zones are determined based on the activity of the catalyst employed in the reaction, and (f) the gas phase exiting the tubular reaction zones is received in the process.

2. The process of claim 1 wherein in (f) the recycled gas has a volume of from about 1,200 to about 6,500 $Nm^3/Nm^3$ of ester per hour.

3. The process of claim 2 wherein the volume of recycled gas is from about 2,000 to about 3,000 $Nm^2/Nm^3$ of ester per hour.

4. The process of claim 1 wherein the tubular reaction zones are in a tube bundle reactor wherein the isothermal conditions are obtained by the use of a cooling or heating fluid.

5. The process of claim 4 wherein the internal diameter of the individual tubes of the reactor is between about 25 and about 400 mm, and the liquid and gas phases are passed through the catalyst in plug flow characteristic.

6. The process of claim 5 wherein the internal diameter of the individual tubes of the reactor is between about 30 and about 100 mm.

7. The process of claim 5 wherein the internal diameter of the individual tubes of the reactor is between about 40 and about 70 mm.

8. The process of claim 1 wherein in (c) from about 0.3 to about 2.0 liters of ester per liter of tubular reaction zone per hour is employed.

9. The process of claim 1 wherein in (d) from about 1.5 to about 15 m$^3$ of ester is sued per m$^2$ cross section of tubular reaction zone per hour.

10. The process of claim 1 wherein the maximum temperature increase in the tubular reaction zones is no greater than about 5° C.

11. The process of claim 10 wherein the temperature increase of no greater than about 5° C. is obtained by either cooling through the use of excess hydrogen in the process, or by external cooling, or by both.

12. The process of claim 1 wherein the reaction temperature is from about 180° C. to about 250° C.

13. The process of claim 1 wherein the process is carried out at a pressure of from a bout 150 to about 280 bar.

14. The process of claim 12 wherein the process is carried out at a pressure of from about 150 to about 280 bar.

15. The process of claim 4 wherein the individual reactor tubes are charged with ester to a uniform accuracy of 5% by means of a two-stage liquid distributor.

16. The process of claim 1 wherein the process is carried out without the addition of methanol.

17. The process of claim 1 wherein the fatty acid methyl esters contain $C_{6-10}$ fatty acid moieties.

18. The process of claim 1 wherein the fatty acid methyl esters contain $C_{12-18}$ fatty acid moieties.

19. The process of claim 1 wherein the fatty acid methyl esters are predominantly unsaturated.

20. A process for the catalytic hydrogenation of liquid saturated and unsaturated $C_{6-24}$ fatty acid methyl esters for the production of saturated fatty alcohols and methanol in the presence of gaseous hydrogen and a hydrogenation catalyst comprising the steps of
A. passing a $C_{6-24}$ fatty acid methyl ester or mixture of such esters and hydrogen gas in co-current flow and without back-mixing through a multiplicity of discrete tubular reaction zones each containing a stationary hydrogenation catalyst at a temperature in the range of from about 160° C. to about 250° C. and at a pressure in the range of from about 50 to about 300 bar while maintaining substantially isothermal conditions in the reaction zones, wherein the flow rate of ester is from about 0.2 to about 2.5 liters of ester per liter of tubular reaction zone per hour and wherein from about 1.5 to about 24 m$^3$ of ester is used per m$^2$ cross section of tubular reaction zone per hour, and
B. recycling the gas phase exiting the tubular reaction zones through step A.

21. The process of claim 20 wherein in step B the recycled gas has a volume of from about 1,200 to about 6,500 Nm$^3$/Nm$^3$ of ester per hour.

22. The process of claim 21 wherein the volume of recycled gas is from about 2,000 to about 3,000 Nm$^3$/Nm$^3$ of ester per hour.

23. The process of claim 20 wherein the tubular reaction zones in step A are in a tube bundle reactor wherein the isothermal conditions are obtained by the use of a cooling or heating fluid.

24. The process of claim 23 wherein the internal diameter of the individual tubes of the reactor is between about 25 and about 400 mm, and the liquid and gas phases are passed through the catalyst packing in plug flow characteristic.

25. The process of claim 20 wherein in step A from about 1.5 to about 15 m$^3$ of ester is sued per m$^2$ cross section of tubular reaction zone per hour.

26. The process of claim 20 wherein in step A the maximum temperature increase in the tubular reaction zones is no greater than about 5° C.

27. The process of claim 26 wherein the temperature increase of no greater than about 5° C. is obtained by either cooling through the use of excess hydrogen in the process, or by external cooling, or by both.

28. The process of claim 23 wherein the individual reactor tubes are charged with ester to a uniform accuracy of 5% by means of a two-stage liquid distributor.

29. The process of claim 20 wherein in step A from about 1.5 to about 15 m$^3$ of ester is used per m$^2$ cross section of tubular reaction zone per hour, the maximum temperature increase in the tubular reaction zones is no greater than about 5° C. and is obtained by either cooling through the use of excess hydrogen in the process or by external cooling or by both, the reaction temperature is from about 180° C. to about 250° C., the reaction pressure is from about 150 to about 280 bar, and in step B the volume of recycled gas is from about 2,000 to about 3,000 Nm$^3$/Nm$^3$ of ester per hour.

30. The process of claim 29 wherein the tubular reaction zones in step A are in a tube bundle reactor having an individual tube internal diameter of from about 40 to about 70 mm.

* * * * *